United States Patent [19]

Satzinger et al.

[11] Patent Number: 4,605,673
[45] Date of Patent: Aug. 12, 1986

[54] 7H-DIBENZO(A,C,)CYCLOHEPTEN-5-ONE-(7) DERIVATIVES

[75] Inventors: Gerhard Satzinger, Denzlingen; Edgar Fritschi; Manfred Herrmann, both of St. Peter, all of Fed. Rep. of Germany

[73] Assignee: Warner-Lambert Company, Morris Plains, N.J.

[21] Appl. No.: 562,690

[22] Filed: Dec. 19, 1983

[30] Foreign Application Priority Data

Dec. 24, 1982 [DE] Fed. Rep. of Germany ....... 3248094

[51] Int. Cl.⁴ ............................................. A61K 31/135
[52] U.S. Cl. .................................. 514/654; 514/227; 514/233; 514/239; 514/240; 514/255; 514/317; 514/651; 544/154; 544/380; 546/204; 564/352; 564/379; 540/484; 540/609
[58] Field of Search ................. 564/352, 379; 424/316, 424/338, 248.4, 300; 514/227, 233, 239, 240, 255, 317, 651; 544/154, 380; 546/204

[56] References Cited

U.S. PATENT DOCUMENTS 3,350,405 10/1967 Schwlenberg et al. ........ 564/352 X
3,389,177 6/1968 Adank et al. ........................ 564/379
3,480,624 11/1969 Fouche ............................ 564/379 X
4,169,897 10/1979 Meyer et al. .................... 564/352 X

OTHER PUBLICATIONS

Theobald et al, "Chemical Abstracts", vol. 67, p. 10863, Section No. 115430r (1968).
Hoffmann La Roche, "Derwent Belgian Patents Report", No. 6/69, p. 8:1 (3/18/67).

Primary Examiner—Robert V. Hines
Attorney, Agent, or Firm—Ronald A. Daignault

[57] ABSTRACT

The invention is concerned with 7H-dibenzo(a,c)-cyclohepten-5-one-(7) derivatives of general formula I

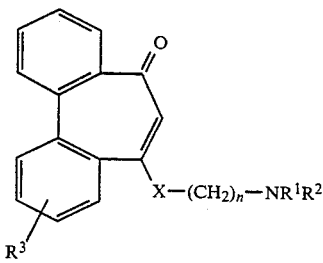

(I)

wherein $R^1$ and $R^2$ can be the same or different, a hydrogen atom, an alkyl radical containing 1 to 3 carbon atoms, or, together with the nitrogen atom to which they are attached form a heterocyclic ring containing 3 to 6 carbon atoms,
n is 2 or 3
$R^3$ is a hydrogen atom or a halogen atom and
X is either a methylene radical or an oxygen atom
and the pharmacologically acceptable salts thereof with inorganic and organic acids.

The invention is furthermore concerned with analogous processes for the preparation thereof and their application for controlling psychic diseases and gastric and/or intestinal ulcers.

9 Claims, No Drawings

7H-DIBENZO(A,C,)CYCLOHEPTEN-5-ONE-(7) DERIVATIVES

SUMMARY OF THE INVENTION

The invention is concerned with new compounds of general formula I

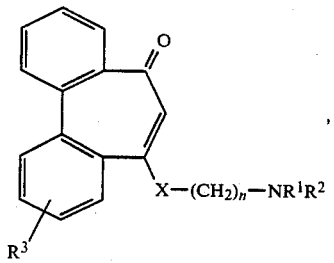
(I)

wherein $R^1$ and $R^2$ can be the same or different and a hydrogen atom, an alkyl radical containing 1 to 3 carbon atoms or, together with the nitrogen atom to which they are attached form a heterocyclic ring containing 3 to 6 carbon atoms, n is 2 or 3, $R^3$ is a hydrogen atom or a halogen atom and X is either a methylene group or an oxygen atom and the pharmacologically acceptable salt thereof with inorganic and organic acids.

The invention also provides a process for the preparation of compounds of general formula I and the pharmacologically acceptable salts thereof, wherein in a compound of general formula II

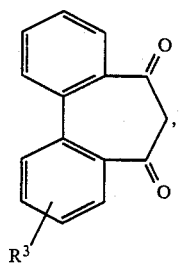
(II)

in which $R^3$ has the aforementioned meaning, is reacted in a previously manner either (a) with Grignard compounds of general formula III

Hal Mg—(CH$_2$)n—NR$^1$R$_2$ (III), in which Hal is a halogen atom and n, $R^1$ and $R^2$ have the aforementioned meanings, or (b) with compounds of general formula IV

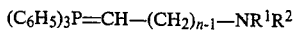

$(C_6H_5)_3P=CH-(CH_2)_{n-1}-NR^1R^2$ (IV), in which n, $R^1$ and $R^2$ have the aforementioned meanings, or (c) with the proviso that when X is to be a methylene group, compounds of general formula V

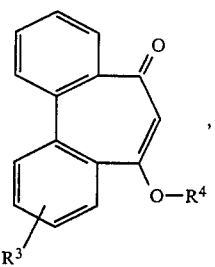
(V)

in which $R^3$ has the aforementioned meaning and $R^4$ is an alkyl radical containing 1 to 3 carbon atoms, are reacted with compounds of general formula IV, or (d) with the proviso that when X is to be an oxygen atom, compounds of general formula II are initially converted by means of strong bases into the corresponding enolates of general formula IV

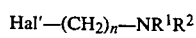

Hal′—(CH$_2$)$_n$—NR$^1$R$^2$ (VI), in which Hal′ is a halogen atom and $R^1$ and $R^2$ have the aforementioned meanings, and if desired, are subsequently converted by means of inorganic or organic acids into the pharmacologically acceptable salts thereof.

The invention also provides pharmaceutical preparations containing as their active substance at least one compound of general formula I or the pharmacologically acceptable salts thereof and, if desired, adjuvants and additives.

A further subject of the invention is the application of compounds of general formula I and the pharmacologically acceptable salts thereof for controlling psychic diseases and gastrointestinal ulcers.

DETAILED DESCRIPTION

For reasons of suitability, the processes (a) to (d) are conducted at temperatures of between 20° C. and 60° C., preferably at around 30° C. The reactant used is, advantageously, an inert organic solvent, for example diethyl ether, benzene, toluene, xylol, tetrahydrofurane, or dimethyl formamide. The new compounds thus obtained of formula I can be isolated in a previously known manner and be purified.

The compounds of formulas II through V used as starting products in the processes, are partially known. The preparation thereof is described, in the case of their not being mentioned in the literature.

Heterocyclic rings within the scope of the invention are saturated five, six, or seven-ring compounds which may contain 3 to 6 carbon atoms and, moreover, also nitrogen, sulphur, or oxygen as heteroatoms. In the event of nitrogen heterocycles with free valence nitrogen, these are substituted by branched or straight-chained lower alkyl radicals, preferably those containing 1 to 3 carbon atoms.

Preferred rings are in the piperidine, morpholine, and N-alkyl piperazine ring, in particular the N-methyl piperazine ring. Hydrogen and Alkyl radicals such as methyl and ethyl are preferred amongst the open ring radicals $R^1$ and $R^2$; n is preferably 2.

Fluorine, chlorine, and bromine are understood as halogen atoms $R^3$; the chlorine atom is preferred.

All halogen atoms, which react under the conditions of Grignard reactions can be used as halogen atoms Hal. The bromine atom is preferred here.

Chlorine, bromine, and iodine atoms are understood as halogen atoms Hal'.

The Grignard compounds of general formula III are prepared in a previously known manner (for example according to Houben-Weyl 13/2a, p. 63 ff. or Rosseels et al., Synthesis 1970, p. 302) from the corresponding alkyl chlorides or alkyl bromides with magnesium.

The compounds of general formula IV can be prepared by means of corresponding triphenyl phosphonium bromides likewise in a previously known manner (e.g. Jap. Pat. No. 78, 150,000).

The conversion of the free bases of general formula I into the pharmacologically acceptable salts thereof is carried out by neutralization with an appropriately applicable organic or inorganic acid, for example, hydrochloric acid, sulphuric acid, phosphoric acid, hydrobromic acid, acetic acid, fumaric acid, oxalic acid, lactic acid, citric acid, malic acid, salicyclic acid, malonic acid, maleic acid, succinic acid, tartaric acid, or ascorbic acid. The active substances are processed for the preparation of pharmaceuticals with the conventional additives and liquid or solid carriers. The compounds of Formula III can be applied orally or parenterally in in liquid or solid form within a wide dose range.

Conventional additives for liquid compositions include, for example, tartrate and citrate buffers, ethanol and complex formers (such as ethylene diaminetetraacetic acid and the nontoxic salts thereof) as well as high molecular weight polymers (such as liquid polyethylene oxide) for regulating the viscosity. Solid carriers include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats, solid high molecular weight polymers (such as polyethylene glycol); if desired, compositions suitable for oral administration can contain flavoring and sweetening agents.

The compounds of general formula I obtained in accordance with the invention possess extraordinary favorable neuropharmacological, in particular antidepressant properties.

Statistics have revealed the great extent of depressive diseases. Studies by the National Institute of Mental Health, Bethesda, USA, showed that approximately 16% of all adults have pathological-depressive symptoms. In pharmacotherapy of depression, tricylic antidepressants represent drugs of first choice, whereby amitryptiline and imipramine are the most widely used. All these antidepressants possess restricting anticholinergic side-effects such as sedation, dryness of the mouth, constipation, drowsiness, dizziness and headaches, tachycardia, impaired vision, ischuria and persisting tremors.

The discovery of new types of antidepressants with few cardiovascular and central side-effects therefore remains an important goal of medical chemistry. The pharmacological results with the compounds of formula I according to the invention indicate that we are dealing here with antidepressants with a psychopharmacological profile unknown up to present. Furthermore the compounds of the invention are surprisingly suitable for the therapy of peptic and duodenal ulcers, which is of great importance in particular on account of the extensive absence of cardial side-effects which are unfortunately typical for classical tricyclic agents. It is worth noticing here that the unexpected intestinal, antisecretory action is not based on anticholinergic mechanisms.

Table I (following) verifies that the compounds of general formula I and the pharmacologically acceptable salts thereof with inorganic or organic acids possess antidepressant properties without sedative, anticholinergic, or circulation-impairing (cardiotoxic) side-effect:

Notes on the Table (A) Reserpine-induced hypothermia in mice is, according to Askew (Life Sci. 2, 725 (1963), a method of studying antidepressive action. The minimal dosage is given which leads to normalization of body temperature measured rectally.

(B) Antidepressants antagonize the lack of drive and passivity towards induced stimuli produced by tetrabenzaine in mice and the assumption and maintenance of abnormal body postures (Arch. Int. Pharmacodyn. Ther. 115, 1–31 (1958). The dosage is given which leads to normalization of the behavior.

(C) The locomotive activity reflects the stimulating or depressive effects on the C.N. system. The spontaneous motility (impulses per minute) was measured in mice by means of photoelectric systems according to Irwin (Rev. Can. Biol. 20, 239 (1961). K in the margin=control, (twice), M=methaqualone (40 m/g i.g.) and S=substance.

(D) The lengthening of the sleeping period is a common in vivo method for the determination of central sedating or stimulating effects. The test animals are mice subsequent to intravenous (IV) injection with 82.5 mg/kg hexobarbital. The influence on the sleeping period under the trial substance is given in % for control purposes.

Side Effects (E) Anticholinergic action measured as mydriasis (mice).

(F) Autonomous test model in dogs after IV catecholamine administration. The tricyclic antidepressants potentiate the blood-pressure effect of noradrenaline and adrenaline in doses which, in themselves, do not have any effect on the blood pressure.

The following comparison trial verifies the antiulcerous action of the compound of Example I:

25 mg/kg (i.g.) substance according to Example I inhibit for instance the gastric secretion in the Shay preparation (H. Shay et al., Gastroenterology 5, p. 43–61 (1945)) by 56%.

80 mg/kg cimetidine (i.g.) inhibit the gastric secretion in the same test system by 45%.

TABLE 1

|  | Amitryptyline | Compounds According to Example Number | | | |
|---|---|---|---|---|---|
|  |  | 1 | 4A | 4B | 4C |
| Toxicity LD$_{50}$ mg/kg | 100 s.c. 200 i.g. | 300 i.g. | 200 i.g. | 200 i.g. | 800 i.g. |
| A | 5 mg/kg s.c. | 5 mg/kg s.c. 20 mg/kg i.g. | 5 mg/kg s.c. 20 mg/kg i.g. | 10 mg/kg s.c. 30 mg/kg i.g. | 75 mg/kg i.g. |
| B | 10 mg/kg s.c. | 10 mg/kg s.c. | 10 mg/kg s.c. | 20 mg/kg s.c. | 75 mg/kg i.g. |

TABLE 1-continued

|  | Amitryptyline | Compounds According to Example Number | | | |
| --- | --- | --- | --- | --- | --- |
|  |  | 1 | 4A | 4B | 4C |
| C | mg/kg s.c. | mg/kg s.c. | mg/kg s.c. | mg/kg s.c. | mg/kg i.g. |
|  | 5 | 5 | 10 | 10 | 150 |
| K | 20 | 20 | 16 | 20 | 19 |
| M | 2 | 2 | 3 | 2 | 6 |
| K | 17 | 17 | 12 | 13 | 15 |
| S | 4 | 20 | 12 | 21 | 19 |
| D | 5 mg/kg s.c. | 5 mg/kg s.c. | 5 mg/kg s.c. | 10 mg/kg s.c. | 150 mg/kg i.g. |
|  | +103% | −42% | ±0% | +11% | ±*0% |
| E | ED$_{50}$ i.g. | up to 75 mg/kg | up to 75 mg/kg | up to 75 mg/kg | up to 200 mg/kg i.g. |
|  | 23.0 mg/kg | s.c. no effect | s.c. no effect | s.c. no effect | no effect |
| F | ED$_{50}$ i.V. | no effect | no effect | no effect | no effect |
|  | 1.0 mg/kg |  |  |  |  |

The data obtained from the animal experiments allow us to assume from experience therapeutic effects in humans with doses of between 20 and 200 mg per day, depending on indication and age. The daily dosage would normally lie between 40 and 150 mg.

The following Examples are given for the purpose of illustrating the invention.

EXAMPLE 1

5-(2-Diethylaminoethoxy)-7H-dibenzo(a,c)cyclohepten-5-one(7).hydrochloride

A solution of 15 g (0.007M) dibenzo(a,c)cyclohepten-5,7-dione is added dropwise to a suspension of 2.4 g 80% sodium hydride in 100 ml anhydrous dimethylformamide (DMFA) at 20° C. under an atmosphere of nitrogen while turbining. After 1.5 hours, a freshly prepared solution of 14 g (0.1M) diethylamino ethyl chloride in 20 ml DMFA is added dropwise thereto; subsequently, this is left to react for five hours at 20° to 25° C. while stirring.

The product is placed into ice water, extracted with ether and the ethereal phase washed twice with water. After removal of the solvent, a residue of 17.0 g remains, which is absorbed in ethyl acetate and precipitated using hydrogen chloride gas as hydrochloride in a fine crystalline form. It is recrystallized from acetonitrile, mp 210°–212° C.

EXAMPLE 2

5-(N-Piperidinoethoxy)-7H-dibenzo(a,c)cyclohepten-5-one(7).hydrochloride

The process is analogous to that described in Example 1, using N-(2-chloroethylpiperidine). The hydrochloride obtained from 5-(N-piperidinoethoxy)-7H-dibenzo(a,c)cyclohepten-5-one(7), mp 222°–223° C.

EXAMPLE 3

5-(N-Morpholinoethoxy)-7H-dibenzo(a,c)cyclohepten-5-one(7).hydrochloride

The preparation is analogous to that described in Example 1, using N-(2-chloroethylmorpholine). The hydrochloride of 5-(N-morpholinoethoxy)-7H-dibenzo(a,c)cycloheptten-5-one(7).hydrochloride is recrystallized from acetonitrile/ethanol=3:2, mp 236° C.

EXAMPLE 4

5-(3-Dimethylaminopropyl)-7H-dibenzo(a,c)cyclohepten-5-one(7) (Ex. 4a)

Variant A

The corresponding Grignard solution is prepared under an atmosphere of nitrogen using 2.4 g (0.1M) activated magnesium chips and 12.2 g (0.1M) freshly distilled dimethylamino propylchloride in 60 ml anhydrous benzene. A solution of 8.4 g (0.04M) dibenzo(a,c)cyclohepten-5,7-dione is added dropwise thereto at 50° C. within ten minutes, while stirring. The preparation is kept under reflux for three hours and then decomposed at 20° C. with a solution of 24 g ammonium chloride in 80 ml water. The organic phase is separated off, extracted with 2N hydrochloric acid and the aqueous extract adjusted to pH 8 using ammonia. The separated product is absorbed in ether; the ether phase is dried over magnesium sulphate. The residue of this phase is dissolved in ethyl acetate and precipitated using oxalic acid. The oxalate of 5-(3-dimethylaminopropyl)-7H-dibenzo(a,c)cyclohepten-5-one(7) is recrystallized from ethyl methylketone, mp 162°–163° C.

Variant B

There is prepared from 50 g triphenylphosphine and 38.5 g 1,3-dibrompropane in 150 ml xylene by heating for 20 hours at 130° C. under nitrogen 80 g crystalline (3-bromopropyl)-triphenylphosphoniumbromide with a melting point of 226° C. This is stirred using a solution of 33 g (0.7M) dimethylamine in 200 ml ethanol for 20 hours at 20°–25° C.) The residue is absorbed after removal of ethanol in a vacuum in 2-propanol and precipitated using hydrogen bromide gas. After recrystallization from ethanol, 43 g (3-dimethylaminopropyl)-triphenylphosphoniumbromide HBr is obtained with a melting point of 279° C.

Twenty-seven grams (0.052M) of this intermediate compound are suspended in 80 ml dry tetrahydrofurane (THF) and converted to the ylide using 65 ml 15% butyllithium solution (0.105M) at 30°–35° C. It is heated under reflux for three hours at 30° C. after addition of 10.5 g (0.05M) dibenzo(a,c)cyclohepten-5,7-dione in 80 ml THF. The batch is decomposed using 15 ml water and the solvent removed on the rotavapor. The residue, treated with 2N hydrochloric acid, yields a crystalline hydrochloride, which is difficult to dissolve, and is recrystallized from ethanol, mp 209° C.

The following compounds are obtained in an analogous manner:

5-(3-Diethylaminopropyl)-7H-dibenzo(a,c)cyclohepten-5-one(7).oxalate (Ex. 4B), mp 125°–126° C. (ethylmethylketone/2-propanol 1:1);

5-(3-methylaminopropyl)-7H-dibenzo(a,c)cyclohepten-5-one(7).oxalate (Ex. 4C), mp 169°–170° C. (ethanol);

5-(3-(4-methyl-1-piperazino-propyl))-7H-dibenzo(a,c)cyclohepten-5-one(7).dioxalate, mp 217°–218° C. (ethanol/water 5:1).

Variant C 5-(3-Dimethylaminopropyl)-7H-dibenzo(a,c)cyclohepten-5-one(7).hydrochloride The reaction of the ylide according to Variant B can also be conducted with an enolether of dibenzo(a,c)cyclohepten-5,7-dione. The enolether is prepared as follows:

A solution of 56 g (0.25M) dibenzo(a,c)cyclohepten-5,7-dione in 900 ml ethanol is mixed with 42 g (0.3M) potassium carbonate. A solution of 37.5 ml diethyl sulphate in 80 ml ethanol is added dropwise thereto while turbining within 30 minutes at 50° C. It is heated for four hours until reflux. After cooling, it is placed on ice and the crystalline precipitate separated off, which is recrystallized from ethanol after drying, mp 133° C. The reaction of 5-ethoxy-7H-dibenzo(a,c)cyclohepten-5-one(7) with the ylide is conducted as described in Variant B.

EXAMPLE 5

3-Chloro-5-(3-diethylaminopropyl)-7H-dibenzo(a,c)cyclohepten-5-one(7).oxalate

One hundred fourty-five grams (0.6M) diphenic acid and 93.5 g (0.3M) $Ag_2SO_4$ are dissolved while stirring in a mixture of 1.2 liter of concentrated sulphuric acid and 120 ml water.

Fourty-two grams gaseous chlorine are then introduced (over a period of approximately 15 hours). It is placed on sufficient ice, the organic product separated off and extracted with one liter of boiling ethanol. After the concentration of the ethanol phase to 400 ml it is diluted with 800 ml hot water. There are obtained 122 g 4-chlorodiphenyl-1,1'-dicarbonic acid, mp 260° C. (benzene).

Seventy-one grams (0.27M) 4-chlorodiphenyl-1,1'-dicarbonic acid are heated with 900 ml triethylamine to 90° C. and mixed within three hours with 57 g (0.35M) malonic acid diethylester. After 2.5 hours at 100° C., it is cooled and the product transferred to ice water. The surface layer is decanted off and the residue recrystallized from 2-propanol. Sixty-six grams (melting point 80° C.) o-diethylmalonylide derivative of the 4-chlorodiphenyl-1,1'-dicarbonic acid anhydride.

Fourty-one grams (0.11M) 4-chlorodiphenyl-1,1'-dicarbonic acid anhydride are heated for 24 hours under reflux in 230 ml formic acid with 10 ml water added. The precipitated oil crystallizes after transfer to ice water. Thirty grams 1'-acetyl-4-chlorodiphenyl-1-carbonic acid with a melting point of 132° C. (benzene/cycohexane 1:1).

In 150 ml anhydrous ethanol, 2.6 g sodium (0.11M) are dissolved. Twenty-six grams (0.1M) of the above compound are introduced and cyclized by heating for six hours under reflux. By transfer to 0.7 l ice water and mixing with 2N hydrochloric acid up to pH 4, there are obtained 23.6 g 3-chlorodibenzo(a,c)cyclohepten-5,7-dione with a melting point of 210°–215° C. This is sufficiently pure to be processed further.

Twenty-three grams (0.09M) 3-chlorodibenzo(a,c)cyclohepten-5,7-dione are dissolved in 400 ml ethanol and converted using 15.5 g (0.11M) potassium carbonate and 15 ml diethyl sulphate in an analogous manner to Example 4, Variant C, into the corresponding enolether, mp 114° C. (cyclohexane).

7.7 g (0.015M) (3-dimethylaminopropyl)-triphenylphosphoniumbromide HBr are prepared in an analogous manner to Example 4, Variant B, under nitrogen and converted into the ylide. After addition of 3.1 g (0.011M) 3-chloro-5-ethoxy-7H-dibenzo(a,c)cyclohepten-5-one(7), dissolved in 25 ml THF, it is heated for another three hours under reflux. Decomposition and reprocessing as described in Example 4, Variant B. The oxalate is precipitated from ethyl acetate and recrystallized from 2-propanol. There is obtained 3-chloro-5-(3-diethylaminopropyl)-7H-dibenzo(a,c)cyclohepten-5-one(7) oxalate with a melting point of 162°–165° C.

We claim:

1. A compound of the formula

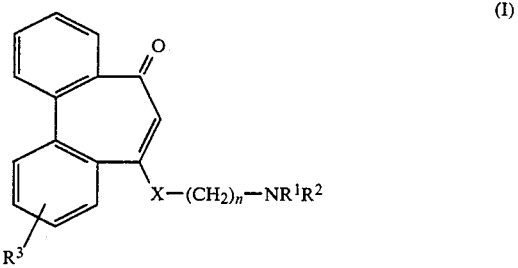

wherein
$R^1$ and $R^2$ are independently hydrogen, an alkyl radical containing 1 to 3 carbon atoms or, together with the nitrogen atom to which they are attached form a heterocyclic ring containing 3 to 6 carbon atoms;
n is 2 or 3;
$R^3$ is a hydrogen atom or a halogen atom, and
X is either a methylene group or an oxygen atom and the pharmacologically acceptable salts thereof with inorganic or organic acids.

2. A compound according to claim 1, wherein the heterocyclic ring containing 3 to 6 carbon atoms is piperidine, morpholine or an N-alkyl-piperazine ring.

3. A compound according to claim 1, wherein $R^1$ and $R^2$ are independently hydrogen, methyl or ethyl.

4. A compound according to claim 1 and being 5-(3-dimethylaminopropyl)-7H-dibenzo(a,c)cyclohepten-5-one(7).

5. A compound according to claim 1 and being 5-(3-diethylaminopropyl)-7H-dibenzo(a,c)cyclohepten-5-one(7).

6. A compound according to claim 1 and being 5-(3-methylaminopropyl)-7H-dibenzo(a,c)cyclohepten-5-one(7).

7. A pharmaceutical preparation comprising as active substance an effective amount of a compound according to claim 1 together with a pharmaceutically acceptable carrier.

8. A method of treating psychic diseases comprising administering an antidepressant effective amount of a pharmaceutical preparation according to claim 7.

9. A method of treating peptic and duodenal ulcers comprising administering an effective amount of a pharmaceutical preparation according to claim 7.

* * * * *